(12) United States Patent
Olapade et al.

(10) Patent No.: US 11,371,345 B2
(45) Date of Patent: Jun. 28, 2022

(54) PREDICTING CLEAN FLUID COMPOSITION AND PROPERTIES WITH A RAPID FORMATION TESTER PUMPOUT

(71) Applicant: Halliburton Energy Services, Inc., Houston, TX (US)

(72) Inventors: Peter Ojo Olapade, Richmond, TX (US); Bin Dai, Spring, TX (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 168 days.

(21) Appl. No.: 16/488,919

(22) PCT Filed: Oct. 5, 2018

(86) PCT No.: PCT/US2018/054689
§ 371 (c)(1),
(2) Date: Aug. 26, 2019

(87) PCT Pub. No.: WO2020/072077
PCT Pub. Date: Apr. 9, 2020

(65) Prior Publication Data
US 2020/0378250 A1 Dec. 3, 2020

(51) Int. Cl.
*E21B 49/08* (2006.01)
*E21B 43/12* (2006.01)
(Continued)

(52) U.S. Cl.
CPC .......... *E21B 49/081* (2013.01); *E21B 43/121* (2013.01); *E21B 49/087* (2013.01);
(Continued)

(58) Field of Classification Search
CPC ... E21B 49/087; E21B 49/0875; E21B 49/088
See application file for complete search history.

(56) References Cited

U.S. PATENT DOCUMENTS

| 2009/0078860 A1 | 3/2009 | Kischkat et al. |
| 2011/0088949 A1 | 4/2011 | Zuo et al. |
| (Continued) | | |

FOREIGN PATENT DOCUMENTS

| WO | 2018144606 | 8/2018 |

OTHER PUBLICATIONS

ISRWO International Search Report and Written Opinion for PCT/US2018/054689 dated Jul. 4, 2019.
(Continued)

*Primary Examiner* — Giovanna Wright
(74) *Attorney, Agent, or Firm* — John Wustenberg; C. Tumey Law Group PLLC

(57) ABSTRACT

A method and system for estimating clean fluid composition and properties. A method may comprise disposing a downhole fluid sampling tool into a wellbore, wherein the downhole fluid sampling tool comprises optical instrumentation, obtaining a fluid sample with the downhole fluid sampling tool, wherein the fluid sample comprises a reservoir fluid contaminated with a well fluid, identifying input parameters from at least one sensor response on the optical instrumentation, and predicting a clean fluid sample of the reservoir fluid using an asymptote of a dimensional reduction analysis and equation of state. A system may comprise a downhole fluid sampling tool and a processing unit. The downhole fluid sampling tool may further comprise an optical instrumentation operable to obtain fluid samples of a reservoir fluid contaminated with a well fluid while the downhole fluid sampling tool is disposed in a wellbore.

22 Claims, 3 Drawing Sheets

(51) Int. Cl.
   *G01N 21/3577*   (2014.01)
   *G01N 21/359*    (2014.01)
   *G01N 33/28*     (2006.01)

(52) U.S. Cl.
   CPC ....... *E21B 49/0875* (2020.05); *G01N 21/359* (2013.01); *G01N 21/3577* (2013.01); *G01N 33/2841* (2013.01)

(56) References Cited

U.S. PATENT DOCUMENTS

| | | |
|---|---|---|
| 2013/0340518 A1 | 12/2013 | Jones et al. |
| 2015/0142317 A1* | 5/2015 | Zuo ..................... E21B 49/088 702/6 |
| 2016/0186559 A1* | 6/2016 | Wang ..................... E21B 49/10 702/6 |
| 2016/0186562 A1 | 6/2016 | Lee et al. |

OTHER PUBLICATIONS

Schlumberger, MDT Modular Formation Dynamics Tester, SMP-5124, Jun. 2002.
Baker Hughes, RCI and IFX Systems provide real-time fluid data and analysis in the North Sea, 2017.
Halliburton, Halliburton Reservoir Description Tool (RDT™) Formation Tester, H012350, Nov. 2016.
Halliburton, Sperry Drilling, GeoTap® IDS Fluid Identification and Sampling Sensor, H013251, May 2019.
Halliburton, Sperry Drilling, GeoTap® Formation Pressure Tester Service, H013325, Jul. 2019.
PCT Application No. PCT/US2018/039829.

* cited by examiner

PREDICTING CLEAN FLUID COMPOSITION AND PROPERTIES WITH A RAPID FORMATION TESTER PUMPOUT

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, plus fraction molecular weight, gas-oil ratios, bubble point, dew point, phase envelope, viscosity, combinations thereof, or the like. Conventional analysis has required transfer of the fluid samples to a laboratory for analysis. Downhole analysis of the fluid sample may also be used to provide real-time fluid properties, thus avoiding delays associated with laboratory analysis.

Accurate determination of fluid properties may be problematic as the fluid sample may often be contaminated with drilling fluids. Fluid samples with levels of drilling fluid contamination may result in non-representative fluids and measured properties. Techniques to determine drilling fluid contamination may include use of pump-out curves, such as density, gas-to-oil ratio and resistivity, among other properties of the fluids. However, determination of drilling fluid contamination using these techniques may be limited, for example, due to lack of significant decrease of the property value, non-linear behavior or properties to contamination levels, and unreliable property measurements. To reduce drilling fluid contamination, longer pump-out time may be required, which may lead to loss of rig time and increase risk of stuck tools, among other problems.

BRIEF DESCRIPTION OF THE DRAWINGS

These drawings illustrate certain aspects of some of the embodiments of the present invention, and should not be used to limit or define the invention.

DETAILED DESCRIPTION

Disclosed herein are methods and systems for predicting contamination level of a fluid sample from a downhole fluid sampling tool. Predicting fluid contamination (e.g., oil based drilling fluid contamination) may then allow right time of sampling and determination of fluid properties of the reservoir fluid, even though the fluid sample was contaminated with well fluid, such as a drilling fluid or other well fluid introduced from the surface. As will be discussed in more detail below, the methods and systems for fluid characterization may use a mathematical algorithm in conjunction with an equation of state to predict fluid contamination and component concentrations of the reservoir fluid, among others. Inputs may include downhole measurements of the fluid sample, including, without limitation, C1, C2, C3, C45 weight percent, gas-oil ratio, oil density (e.g., live oil or dead oil density), and/or bubble point. Inputs may further include a mud filtrate composition.

For example, due to overbalance pressure in the wellbore, drilling fluid invades the formation in the vicinity of the wellbore during drilling. Unlike water-based mud (WBM), oil-based mud (OBM) is miscible with the formation fluid and therefore changes the composition and the properties of the original formation fluid. Before taking samples, the contaminated fluid may be pumped out first. The pump out fluid may include mud filtrate initially, but may become cleaner as the pumping progresses. The composition and properties measured by an optical sensor during pumpout may be for contaminated fluid. Since OBM alters fluid properties, fluid composition and properties may not be representative of the original formation fluid, especially at the early pumpout stage when mud filtrate contamination level may be higher than 20 percent of the formation fluid. The Gas Oil Ratio "GOR" of the original formation fluid may be known to be higher than that of the contaminated fluid and the bubble point pressure of the original formation fluid may be higher than that of the contaminated fluid. Unless the contamination level may be less than 5 percent of the formation fluid low, measured optical fluid properties may be representative of a pure formation fluid. The composition measured by downhole optical tools may be that of contaminated fluid because at the end of the pumpout, the contamination level may be low but it may not be zero.

Figure 1:
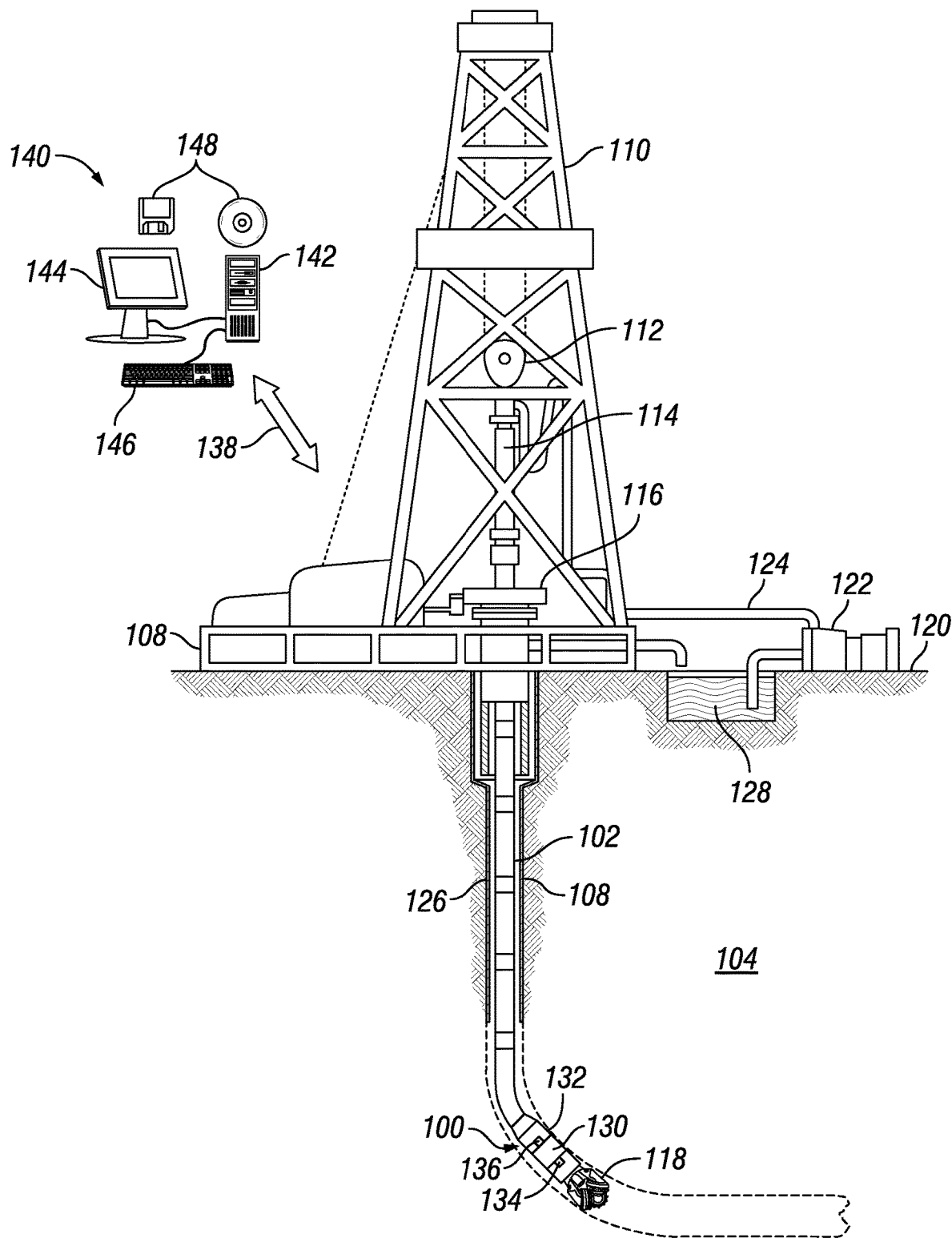
FIG. 1 is a schematic diagram of an example downhole fluid sampling tool on a drill string.

FIG. 1 is a schematic diagram is shown of downhole fluid sampling tool 100 disposed on a drill string 102. The downhole fluid sampling tool 100 may be used to obtain a fluid sample, for example, a fluid sample of a reservoir fluid from subterranean formation 104. The reservoir fluid may be contaminated with well fluid (e.g., drilling fluid) from wellbore 106. As described herein, the fluid sample may be analyzed to determine fluid contamination and other fluid properties of the reservoir fluid. As illustrated, a wellbore 106 may extend through subterranean formation 104. While the wellbore 106 is shown extending generally vertically into the subterranean formation 104, the principles described herein are also applicable to wellbores that extend at an angle through the subterranean formation 104, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 108 may support a derrick 110 having a traveling block 112 for raising and lowering drill string 102. Drill string 102 may include, but is not limited to, drill pipe and coiled tubing, as generally known to those skilled in the art. A kelly 114 may support drill string 102 as it may be lowered through a rotary table 116. A drill bit 118 may be attached to the distal end of drill string 102 and may be driven either by a downhole motor and/or via rotation of drill string 102 from the surface 120. Without limitation, drill bit 118 may include, roller cone bits, PDC bits, natural diamond bits, any hole openers, reamers, coring bits, and the like. As drill bit 118 rotates, it may create and extend wellbore 106 that penetrates various subterranean formations 104. A pump 122 may circulate drilling fluid through a feed pipe 124 to kelly 114, downhole through interior of drill string 102, through orifices in drill bit 118, back to surface 120 via annulus 126 surrounding drill string 102, and into a retention pit 128.

Drill bit 118 may be just one piece of a downhole assembly that may include one or more drill collars 130 and downhole fluid sampling tool 100. Downhole fluid sampling tool 100, which may be built into the drill collars 130) may gather measurements and fluid samples as described herein. One or more of the drill collars 130 may form a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may be used to collect a fluid sample from subterranean formation 104. As previously described, the fluid sample may comprise a reservoir fluid, which may be contaminated with a well fluid. The downhole fluid sampling tool 100 may obtain and separately store different fluid samples from subterranean formation 104. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100.

The downhole fluid sampling tool 100 may further include a fluid analysis module 136. In examples, the fluid analysis module 136 may comprise an optical instrumentation, such as an optical sensor, that may continuously monitor a reservoir fluid. The fluid analysis module 136 may be operable to derive properties and characterize the fluid sample. By way of example, the fluid analysis module 136 may measure absorption spectra and translate such measurements into component concentrations of the fluid sample, which may be lumped component concentrations, as described above. The fluid analysis module 136 may also measure gas-to-oil ratio, live fluid density, live fluid viscosity, formation pressure, and formation temperature. The fluid analysis module 136 may also be operable to determine fluid contamination of the fluid sample. The fluid analysis module 136 include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 136 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to the surface 120. As illustrated, a communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that can store code representative of the methods described herein. The information handling system 140 may act as a data acquisition system and possibly a data processing system that analyzes information from downhole fluid sampling tool 100. For example, information handling system 140 may process the information from downhole fluid sampling tool 100 for determination of fluid contamination. The information handling system 140 may also determine additional properties of the fluid sample (or reservoir fluid), such as component concentrations, pressure-volume-temperature properties (e.g., bubble point, phase envelop prediction, etc.) based on the fluid characterization. This processing may occur at surface 120 in real-time. Alternatively, the processing may occur at surface 120 or another location after recovery of downhole fluid sampling tool 100 from wellbore 106. Alternatively, the processing may be performed by an information handling system in wellbore 106, such as fluid analysis module 136. The resultant fluid contamination and fluid properties may then be transmitted to surface 120, for example, in real-time.

Figure 2:
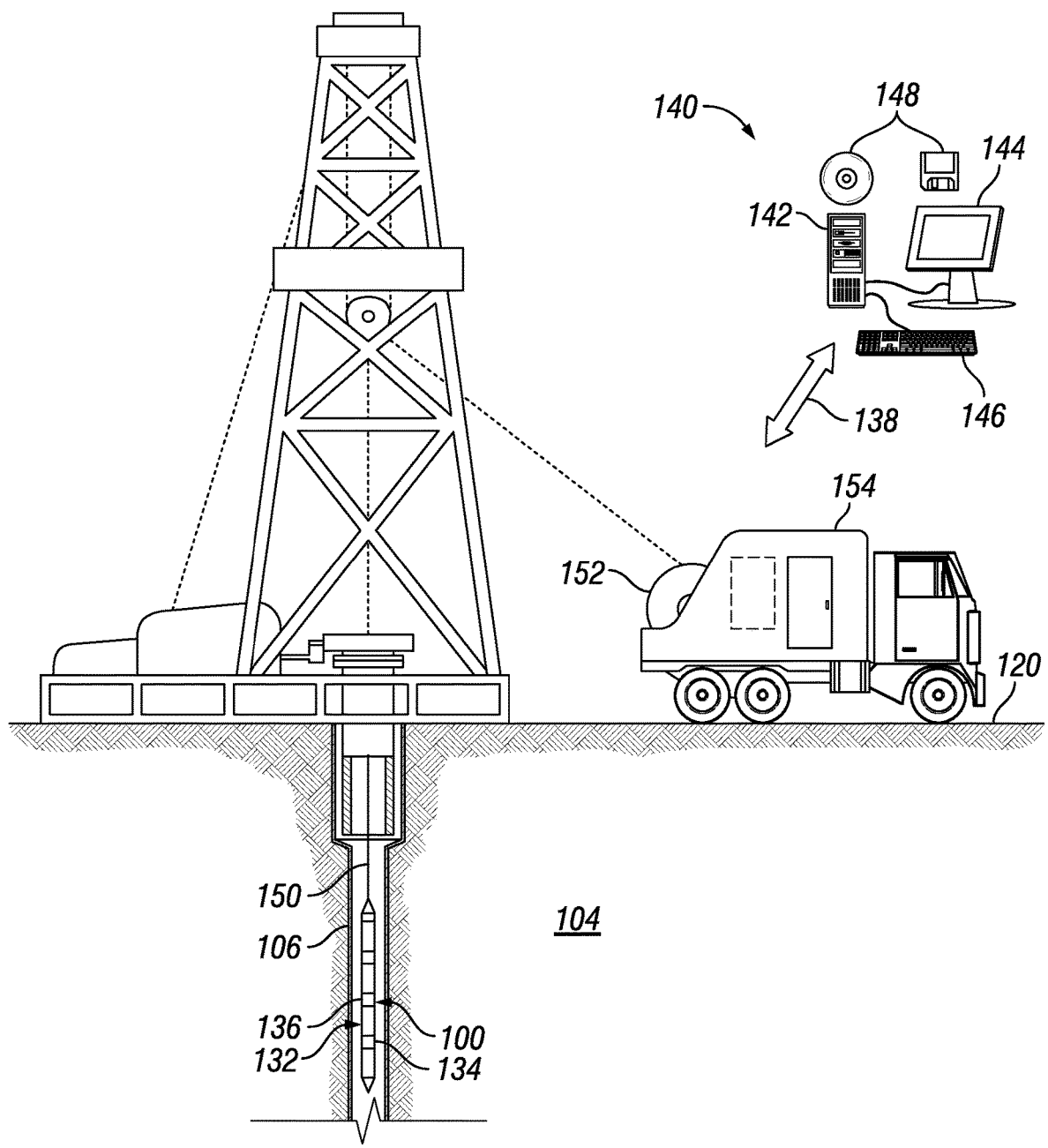
FIG. 2 is a schematic diagram of an example downhole fluid sampling tool on a wireline.

Referring now to FIG. 2, a schematic diagram is shown of downhole fluid sampling tool 100 on a wireline 150. As illustrated, wellbore 106 may extend through subterranean formation 104. Downhole fluid sampling tool 100 may be similar in configuration and operation to downhole fluid sampling tool 100 shown on FIG. 1 except that FIG. 2 shows downhole fluid sampling tool 100 disposed on wireline 150. It should be noted that while FIG. 2 generally depicts a land-based drilling system, those skilled in the art will readily recognize that the principles described herein are equally applicable to subsea drilling operations that employ floating or sea-based platforms and rigs, without departing from the scope of the disclosure.

As illustrated, a hoist 152 may be used to run downhole fluid sampling tool 100 into wellbore 106. Hoist 152 may be disposed on a recovery vehicle 154. Hoist 152 may be used, for example, to raise and lower wireline 150 in wellbore 106. While hoist 152 is shown on recovery vehicle 154, it should be understood that wireline 150 may alternatively be disposed from a hoist 152 that is installed at surface 120 instead of being located on recovery vehicle 154. Downhole fluid sampling tool 100 may be suspended in wellbore 106 on wireline 150. Other conveyance types may be used for conveying downhole fluid sampling tool 100 into wellbore 106, including coiled tubing and wired drill pipe, for example. Downhole fluid sampling tool 100 may comprise a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may also include a fluid analysis module 136, which may be operable to process information regarding fluid sample, as described above with respect to FIG. 1. The downhole fluid sampling tool 100 may be used to collect fluid samples from subterranean formation 104. The downhole fluid sampling tool 100 may obtain and separately store different fluid samples from subterranean formation 104.

As previously described, information from downhole fluid sampling tool 100 may be transmitted to an information handling system 140, which may be located at surface 120. As illustrated, communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that may store code representative of the methods described herein. In addition to, or in place of processing at surface 120, processing may occur downhole (e.g., fluid analysis module 136). In examples, information handling system 140 may perform computations to estimate clean fluid composition.

Figure 3:
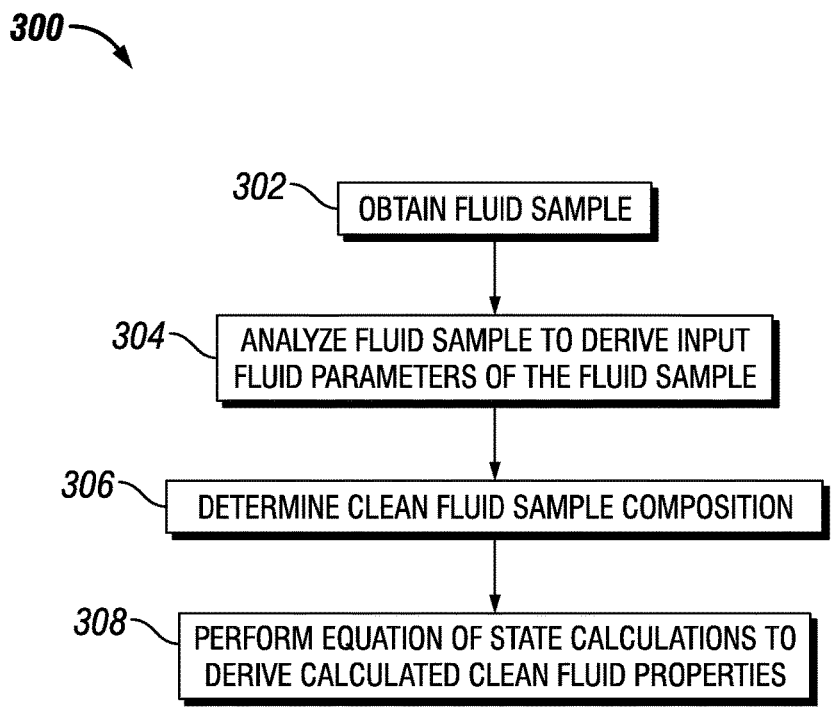
FIG. 3 is a flow chart for predicting clean fluid samples.

FIG. 3 shows a flow chart of an example of a method 300 for predicting clean fluid composition. The method 300 may be implemented using the systems implemented on FIGS. 1 and 2, for example, predict clean fluid composition (e.g., drilling fluid contamination) of a fluid sample. Method 300 may be implemented at surface 120 or in wellbore 106. By way of example, fluid analysis module 136 of downhole fluid sampling tool 100 may include a processing unit (e.g., a microprocessor, etc.) that may be operable to implement one or more of the method steps of method 300. By way of further example, information handling system 140 may also include a processing unit 142 (e.g., a microprocessor, etc.) that can be operable to implement one or more of the method steps of method 156. As will be appreciated, processing may occur either in wellbore 106, at surface 120, at a remote location, or a combination of these locations.

In step 302, fluid sample may be obtained. The fluid sample may be a fluid sample from a reservoir of interest, for example, from subterranean formation 104 shown on FIGS. 1 and 2. Any suitable technique may be used to obtain fluid sample. As described previously, downhole fluid sampling tool 100 may be used to collect fluid sample on a drill string 102 (e.g., FIG. 1) or on a wireline 150 (e.g., FIG. 2), for example. For example, downhole fluid sampling tool 100 may be operated to obtain a fluid sample. The fluid sample may be contaminated with a well fluid, such as drilled fluid. The fluid sample may be obtained at formation temperature and pressure. It should be understood that downhole fluid sampling tool 100 is merely illustrative of one example apparatus that may be used in obtaining a fluid sample and those of ordinary skill in the art should be able to select an appropriate apparatus and associated methodology to obtain a fluid sample. The fluid sample need not necessarily be collected downhole. By way of example, the techniques described herein may be used to characterize the fluid sample of a produced fluid that may be obtained at surface 120. After fluid sample is obtained, subsequent processing steps, discussed below, may occur at surface 120 or in wellbore 106. Alternatively, fluid sample may be transferred to a remote location for one or more of the subsequent processing steps.

In step 304, the fluid sample may be analyzed to derive input parameters that characterize the fluid sample. Without limitation, the input parameters may be obtained from measurements of the fluid sample. The measurements may be performed in wellbore 106, at surface 120, or at a remote location. The downhole fluid sampling tool 100 or other suitable formation evaluation tools may be used to analyze the fluid sample. Any measuring instrument capable of producing a measurable response to the change of the fluid property may be used.

The measuring instrument may contain a detector and/or sensor detecting, for example, density, resistivity/conductivity, viscosity, chromatography, radioactivity, dielectric constant, optical density, magnetic resonance, weight, acoustic impedance, acoustic velocity, optical response, diffusion coefficients, molecular weight, refractive index at various wavelengths, and combinations thereof. One or more sensors or detectors (e.g. sensor 134 of downhole fluid sampling tool 100 shown on FIG. 1) may be used in the measuring instrument.

The input parameters of the fluid sample that may be derived may include fluid properties that may be obtained from measurements of the fluid sample, including, without limitation, one or more of component concentrations (e.g., weight %, etc.), gas-to-oil ratio, live oil density (or dead oil density) and bubble point. Additional fluid properties that may be derived may include one or more of volume fraction of water, API gravity, live oil viscosity, formation temperature, or formation pressure, among others. The component concentrations obtained from these measurements may typically be a lumped component concentration with concentration of heavier hydrocarbons lumped together. By way of example, the component concentration may be provided showing fractions of carbon dioxide ($CO_2$), methane ($CH_4$), ethane ($C_2H_6$), propane ($C_3H_8$), butane ($C_4H_{10}$), pentane ($C_5H_{12}$), and the C6+ group. The C6α group may include the concentration of all hydrocarbons with six or more carbon atoms lumped into a single component concentration. In some instances, the C5 hydrocarbons may not be separately reported, with the C5+ hydrocarbon group lumped into a single component concentration. Moreover, some of the lower hydrocarbons, such as the C3, C4, or C5 hydrocarbons may also be grouped and reported together, for example, C3-C4 hydrocarbon group, C3-C5 hydrocarbon group, and/or C4-C5 hydrocarbon group. These concentrations may be provided as weight or mole percentages. "Live oil" typically refers to an oil at reservoir conditions. A fluid sample at reservoir conditions may be referred as "live oil." The live oil density of the fluid sample may be obtained from measurements at reservoir conditions. Without limitation, the live oil density may be obtained using a density sensor, for example, on downhole fluid sampling tool 100. The bubble point may include the temperature and pressure at which the first bubble of gas comes out of the fluid sample. Without limitation, the bubble point may be obtained either from measurement or derived from empirical correlation. Without limitation, the gas-to-oil ratio may be obtained by measuring the quantity of vapor component and liquid components of crude oil using near infrared absorption peaks. The ratio of methane to the oil peak on a single phase live crude oil may be directly related to gas-to-oil ratio.

Additional input parameters may also include mud filtrate composition. The term "mud filtrate" typically refers to the liquid part of a drilling fluid, for example, that passes through filter cake. Any suitable method may be used to derive the mud filtrate composition, including a mud log.

In step 306, the composition of a clean fluid sample may be determined. The clean fluid sample composition may be determined by a mathematical algorithm. The composition determined in step 306 may be the composition of a predicted clean fluid sample. In other words, the composition may the composition of the reservoir fluid contaminated with the well fluid (e.g., drilling fluid). Without limitation, an algorithm to estimate clean fluid composition and properties may use an asymptote of a principal component analysis (PCA), which may allow for an equation of state to be developed. A principal component analysis is one method of dimensional reduction and is linear in form. Other linear methods of dimension reduction include singular value decomposition, also linear in form and wavelet analysis which is nonlinear in form. The disclosed method may be described by a principal component analysis, but it should be understood that other methods of dimensional reduction may be used including but not limited to those described. The inputs to the algorithm may be optical responses of an integrated computational element (ICE). Each ICE core may be designed such that one particular fluid component or properties may be accentuated in the detector response while muting all other additional information recorded by downhole fluid sampling tool 100. In examples, sensor response signals may first be despiked using a filter and moving window averaging method. Data is first despiked using outlier detection filter method such as Hampel filter and then moving average method is applied to the data. Window size is set for both filter method and moving average method.

Next, the sensor signals may be transformed by a Principal Component Analysis (PCA).

Figure 4:
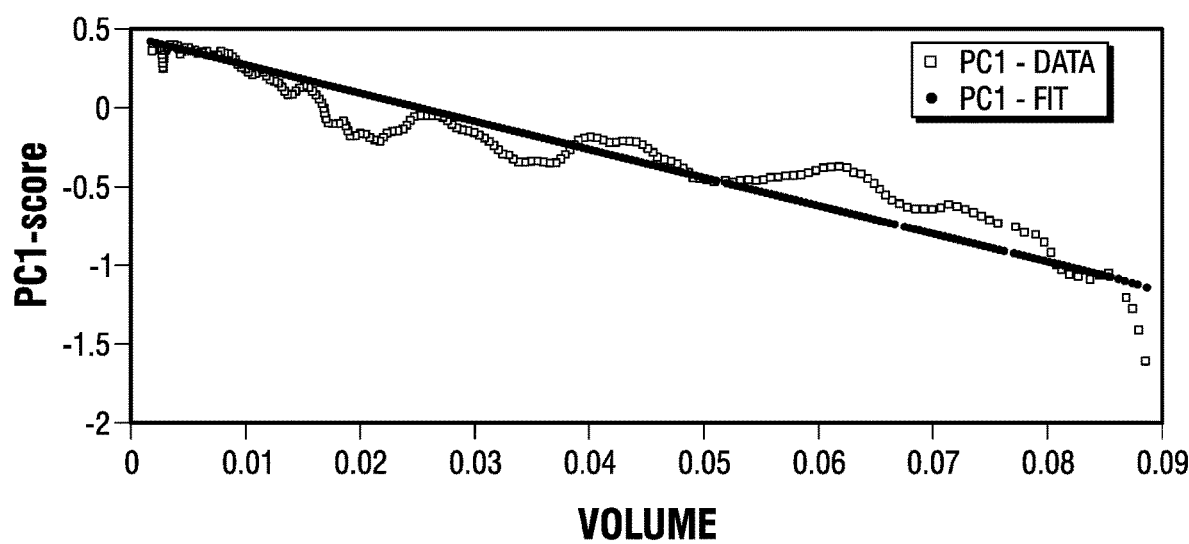
FIG. 4 is a chart illustrating a plot of Principle Component Scores verse volume.

The PCA reduces a high dimensional dataset, comprising more than 30 individual data sets, to a low dimensional set, comprising 2 to 3 individual data sets, of features. Dimensional data sets may be sensor signals. Every sensor signal is a measurement of the optical response of a particular fluid component or fluid property. The reduction may be performed without loss, or error in the transmission of data, off information from the original dataset. In examples, a robust principal component analysis (RPCA) may be chosen and unlike the classical PCA, RPCA may be resistant to outliers in a dataset, the dataset referring to optical sensor data. The outliers identified by the RPCA may be excluded from the PCA scores and loadings. A robust regression method may also be applied to PCA scores to compute scores fit as follows:

$$\text{scores}_{fit} = A + B \, Xv^{-\beta} \quad (1)$$

Where A and B are constants to be determined by a regression method. The variables A and B are determined using a constraint optimization method. The variable v is the formation fluid pumpout accumulated volume and β is the density decay rate and may be obtained by performing an optimization on the density dataset using a nonlinear constrained optimization method. Similar to RPCA, robustfit regression method may be less sensitive to outliers in a dataset. The outliers identified by the robustfit regression method may also be excluded from the PCA scores and loadings. The asymptote of the fit to PCA scores shown in Equation (1) may be obtained as when accumulated volume, v is infinitely large. As an example, FIG. 4 shows a graph where the score of the first principal component (PC1) and a fit for a dataset. The score is plotted against volume $-\beta$. At infinitely large volume, volume $-\beta$ may be zero and a projected value of the fit to a PC score when volume $-\beta$ equals zero may be used as the estimate of a clean sensor data set of the PC score.

Then the clean sensor data set may be inverted from an asymptote of the PCA scores fit and the PCA loadings. PCA loadings are the coefficient that transforms the PCA scores (optical data in the PCA space) back to the original dataset. The PCA score is a linear combination of the original dataset. The coefficient that the scores are multiplied with to get the original dataset is the loadings. Using a machine-learning algorithm, the concentration of the fluid components: methane (C1), ethane (C2), propane (C3), butane and pentane combined (C4-C5), and C6+ may be estimated in-situ from the clean sensor data set. The molecular weight and the density of C6+ may be estimated by a predictive machine learning method such as K-nearest neighbor ("KNN"). The live oil density, GOR, and bubble point pressure may be computed using the clean fluid composition and cubic equation of state.

Referring back to FIG. 3, in step 308, equation of state calculations may be performed to derive calculated clean fluid properties. Equation of state flash calculations may be used to derive the gas to oil ratio and dead oil density, among other fluid properties, of the fluid sample. Equation of state calculations may be used to derive the phase envelope and bubble point of the fluid sample, among other properties. To reduce the computational complexity of the equation of state calculations, the component mole fractions of the fluid sample may be lumped, for example, to C1, C2, . . . , C34, C35, and C36+ mole fractions. The calculated fluid properties determined by the equation of state flash calculations may include one or more of gas-to-oil ratio, dead oil density, bubble point, and/or phase envelope, for example. "Dead oil" typically refers to an oil at sufficiently low pressure that it contains substantially no dissolved gas or relatively thick oil that has lost its volatile components. Additional calculated fluid properties may include, without limitation, liquid mole fraction distribution, vapor mole fraction distribution, the density, molecular weight and mole volume for the liquid and vapor portion of the live oil.

The equation of state calculations may be based on equation of state equations that represent the functional relationship between pressure, volume, and temperature of the fluid sample. Equations of states may be used to predict physical properties, such as macroscopic pressure-volume-temperature properties, including bubble point, dew point, phase envelope, viscosity, gas-to-oil ratio, density, combinations thereof.

Equation of state calculations may use information or properties such as temperature, pressure, and composition. For example, one simple equation of state is PV=nRT, known as the ideal gas law, where P=pressure, V=volume, n=moles, R=Ideal Gas Constant (also used for units conversion), and T=absolute temperature (Kelvin or Rankine). When the physical properties and composition of the reservoir fluid under a given set of conditions are known, the behavior of the reservoir fluid at other pressures and temperatures may be predicted. Equations of state that may be used may include, for example, expansions of the ideal gas law to account for individual molecular compositions. According to some embodiments, they are third order equations. Any of a variety of equations of state may be used. The equation of state may be cubic or non-cubic. The equation of state may vary depending on or more compositional components of the fluid sample. The equations of state have many names, as they have been modified to improve the match between predicted and observed behavior. Without limitation, the equation of state may be selected from one or more of Boyle, Van der Waals, Redlich-Kwong, Soave-Redlich-Kwong, Peng-Robinson, Peng-Robinson-Stryjek-Vera, Patek-Teja, Schmit-Wenzel, or Esmaeilzadeh-Roshanfekr.

TABLE 1

| Statistics | End Volume (L) | C1(g/cc) | C2(g/cc) | C3(g/cc) | C4C5(g/cc) | C6(g/cc) | LOD(g/cc) | GOR(scf/bbl) | Bubblepoint(psi) |
|---|---|---|---|---|---|---|---|---|---|
| | 198 | 0.08954 | 0.00015 | 0.0009 | 0.01745 | 0.53262 | 0.71038 | 1078.55 | 2466.66 |
| | 150 | 0.0910 | 0.00016 | 0.00088 | 0.01842 | 0.52998 | 0.70687 | 1103 | 2487.87 |
| | 100 | 0.09332 | 0.00017 | 0.00084 | 0.01961 | 00.52848 | 0.70163 | 1129.2 | 2493.81 |
| | 50 | 0.09492 | 0.00013 | 0.00096 | 0.01566 | 0.5334 | 0.70167 | 1139.96 | 2550.8 |
| Relative Standard Deviation | | 2.581866 | 11.19885 | 5.586592 | 9.38712917 | 0.43096285 | 0.60617958 | 2.475281096 | 1.438171192 |
| % difference between 198 L and 50 L | | 5.667931 | −15.3846 | 6.25 | −11.430396 | 0.14623172 | −1.2413243 | 5.387031124 | 3.298572997 |

Table 1 is the predicted clean fluid and properties at different pumpout end volumes. As seen in Table 1, the clean fluid composition and properties predicted at pumpout end volume of fifty (50) liters may not significantly differ from those predicted at one hundred and ninety eight (198) liters. Additionally, analysis of PC1 shows that most of the variation in the optical data occurs within the first few tens of liters during pumpout. This may allow an operator to determine when and where to draw clean samples in a less time and with less pumpout.

After collecting clean samples with downhole fluid sampling tool 100 (e.g., FIG. 1 or FIG. 2). An operator may make a production or completion decision based at least in part on the measurements and information collected from the clean samples. For example, production or completion decisions may be choosing material used in Facilities design [$H_2S$, gas/oil ratio (GOR), corrosion, and scaling], determining flow assurance remediation strategy (i.e., introduction of hydrate, wax, asphaltene into a wellbore), creating reservoir simulation input (EOS modeling), and determining enhanced oil recovery based on a fluid type.

Distinctive improvements over current methods may be the ability to estimate clean fluid compositions, such as methane (C1), ethane (C2), propane (C3), butane and pentane combined (C4-C5), and C6+ using PCA asymptote in real-time. Additional improvements may allow for using clean fluid composition and an equation of state to estimate bubble point and GOR at downhole condition in real time. Current methods measure few discreet bubble points of contaminated fluid while the proposed method, disclosed above, may predict clean fluid bubble point at pumpout end volume as low as forty (40) liters. Clean bubble point provides a pumping rate limit to maintain reservoir fluid in monophasic condition. Currently, optical tools may predicts composition and some properties of contaminated fluid. This solution may enable an operator to predict clean fluid composition and properties such as GOR and bubble point in real time.

This may be possible due to clean fluid bubble points may be higher than that of contaminated fluid. Clean fluid bubble points provide the limit for a pumping rate during pumpout. Improvements may also allow for an ability to predict formation composition at low pumpout end volume even before taking samples. This enables an operator to perform rapid pumpout (pumping fluid for as short as 20-25 mins) at different depths for the purpose of determining reservoir continuity.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

Statement 1. A method for estimating clean fluid composition and properties may comprise disposing a downhole fluid sampling tool into a wellbore, wherein the downhole fluid sampling tool comprises optical instrumentation, obtaining a fluid sample with the downhole fluid sampling tool, wherein the fluid sample comprises a reservoir fluid contaminated with a well fluid, identifying input parameters from at least one sensor response on the optical instrumentation, wherein the input parameters comprise fluid properties obtained from measurement of the fluid sample and mud filtrate composition, and predicting a clean fluid sample of the reservoir fluid using an asymptote of a dimensional reduction analysis and equation of state.

Statement 2. The method of statement 1, further comprising despiking the at least one sensor response.

Statement 3. The method of statements 1 or 2, wherein the despiking an original dataset is performed by a Hampel filter.

Statement 4. The method of statements 1 to 3, further comprising transforming the at least one sensor response by a principal component analysis.

Statement 5. The method of statements 1 to 4, further comprising performing a robust principal component analysis on the at least one sensor response.

Statement 6. The method of statements 1 to 5, further comprising applying a robust regression method on the at least one sensor response, wherein the robust regression method is computed as $scores_{fit}=A+B \times v^{-\beta}$ where A and B are constants determined by a regression method, v is a formation fluid pumpout accumulated volume, and μ is a density decay rate.

Statement 7. The method of statements 1 to 6, further comprising performing a production or completion decision.

Statement 8. The method of statements 1 to 7, wherein the well fluid comprises a drilling fluid.

Statement 9. The method of statements 1 to 8, wherein obtaining the fluid sample comprising operating the downhole fluid sampling tool in the wellbore to obtain the fluid sample.

Statement 10. A method to estimate clean fluid composition may comprise despiking an original dataset, applying a robust regression method on at least one sensor response, wherein the robust regression method is computed as $scores_{fit}=A+B \times v^{-\beta}$, where A and B are constants determined by a regression method, v is a formation fluid pumpout accumulated volume, and β is a density decay rate, removing a contaminated reservoir fluid, and performing a pumpout to remove clean reservoir fluid from the wellbore.

Statement 11. The method of statement 10, wherein the despiking the original dataset is performed by a Hampel filter.

Statement 12. The method of statements 10 or 11, further comprising performing a robust principal component analysis on the original data set.

Statement 13. The method of statements 10 to 12, further comprising transforming the original data set by a principal component analysis.

Statement 14. The method of statements 10 to 13, further comprising fitting an asymptote to the clean sensor data set.

Statement 15. A system for estimating clean fluid composition may comprise a downhole fluid sampling tool comprising optical instrumentation operable to obtain fluid samples of a reservoir fluid contaminated with a well fluid while the downhole fluid sampling tool is disposed in a wellbore, and a processing unit configured to: predict a clean fluid sample of the reservoir fluid from at least one sensor response on the optical instrumentation using an asymptote of a principal component analysis and equation of state.

Statement 16. The system of statement 15, wherein the processing unit is further configured to despike the at least one sensor response.

Statement 17. The system of statement 16, wherein a Hampel filter is used to despike the at least one sensor response.

Statement 18. The system of statements 15 to 17, wherein the processing unit is further configured to transform the at least one sensor response to a principal component analysis space.

Statement 19. The system of statements 15 to 18, wherein the processing unit is further configured to perform a robust principal component analysis on the at least one sensor response.

Statement 20. The system of statements 15 to 19, wherein the processing unit is further configured to apply a robust regression method on the at least one sensor response, wherein the robust regression method is computed as $scores_{fit}=A+B \times v^{-\beta}$, where A and B are constants determined by a regression method, v is a formation fluid pumpout accumulated volume, and β is a density decay rate.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method for estimating clean fluid composition and properties, comprising:
   disposing a downhole fluid sampling tool into a wellbore, wherein the downhole fluid sampling tool comprises optical instrumentation;
   obtaining a fluid sample with the downhole fluid sampling tool;
   performing a rapid pumpout operation with as low as 40 liters of pumpout volume or 20-25 minutes of pumpout time;
   identifying input parameters from at least one sensor response on the optical instrumentation, wherein the input parameters comprise fluid properties obtained from measurement of the fluid sample and mud filtrate composition; and
   predicting a clean fluid sample of the reservoir fluid using an asymptote of a dimensional reduction analysis and equation of state.

2. The method of claim 1, further comprising despiking the at least one sensor response.

3. The method of claim 2, wherein the despiking the at least one sensor response is performed by a Hampel filter.

4. The method of claim 1, further comprising transforming the at least one sensor response by a principal component analysis.

5. The method of claim 1, further comprising performing a robust principal component analysis on the at least one sensor response.

6. The method of claim 5, further comprising applying a robust regression method on the at least one sensor response, wherein the robust regression method is computed as $scores_{fit}=A+B \times v^{\beta}$, where A and B are constants determined by a regression method, v is a formation fluid pumpout accumulated volume, and β is a density decay rate.

7. The method of claim 1, further comprising performing a production or completion decision.

8. The method of claim 1, wherein the well fluid comprises a drilling fluid.

9. The method of claim 1, wherein obtaining the fluid sample comprising operating the downhole fluid sampling tool in the wellbore to obtain the fluid sample.

10. A method to estimate clean fluid composition, comprising:
    despiking an original dataset,
    applying a robust regression method on at least one sensor response, wherein the robust regression method is computed as $scores_{fit}=A+B \times v^{\beta}$, where A and B are constants determined by a regression method, v is a formation fluid pumpout accumulated volume, and β is a density decay rate;
    removing a contaminated reservoir fluid; and
    performing a pumpout to remove clean reservoir fluid from the wellbore.

11. The method of claim 10, wherein the despiking the original dataset is performed by a Hampel filter.

12. The method of claim 10, further comprising performing a robust principal component analysis on the original data set.

13. The method of claim 10, further comprising transforming the original data set by a principal component analysis to form a clean sensor data set.

14. The method of claim 13, further comprising fitting an asymptote to the clean sensor data set.

15. A system for estimating clean fluid composition, comprising:
a downhole fluid sampling tool comprising optical instrumentation operable to:
obtain fluid samples of a reservoir fluid while the downhole fluid sampling tool is disposed in a wellbore;
perform a rapid pumpout operation with as low as 40 liters of pumpout volume or 20-25 minutes of pumpout time;
a processing unit configured to:
predict a clean fluid sample of the reservoir fluid from at least one sensor response on the optical instrumentation using an asymptote of a principal component analysis and equation of state.

16. The system of claim 15, wherein the processing unit is further configured to despike the at least one sensor response.

17. The system of claim 16, wherein a Hampel filter is used to despike the at least one sensor response.

18. The system of claim 15, wherein the processing unit is further configured to transform the at least one sensor response to a principal component analysis space.

19. The system of claim 15, wherein the processing unit is further configured to perform a robust principal component analysis on the at least one sensor response.

20. The system of claim 15, wherein the processing unit is further configured to apply a robust regression method on the at least one sensor response, wherein the robust regression method is computed as $scores_{fit}=A+B \times v^{\beta}$, where A and B are constants determined by a regression method, $v$ is a formation fluid pumpout accumulated volume, and $\beta$ is a density decay rate.

21. A method for estimating clean fluid composition and properties, comprising:
disposing a downhole fluid sampling tool into a wellbore, wherein the downhole fluid sampling tool comprises optical instrumentation;
obtaining a fluid sample with the downhole fluid sampling tool, wherein the fluid sample comprises a reservoir fluid contaminated with a well fluid;
identifying input parameters from at least one sensor response on the optical instrumentation, wherein the input parameters comprise fluid properties obtained from measurement of the fluid sample and mud filtrate composition;
performing a robust principal component analysis on the at least one sensor response;
applying a robust regression method on the at least one sensor response, wherein the robust regression method is computed as $scores_{fit}=A+B \times v^{\beta}$, where A and B are constants determined by a regression method, $v$ is a formation fluid pumpout accumulated volume, and $\beta$ is a density decay rate;
predicting a clean fluid sample of the reservoir fluid using an asymptote of a dimensional reduction analysis and equation of state.

22. A system for estimating clean fluid composition, comprising:
a downhole fluid sampling tool comprising optical instrumentation operable to obtain fluid samples of a reservoir fluid contaminated with a well fluid while the downhole fluid sampling tool is disposed in a wellbore; and
a processing unit configured to:
predict a clean fluid sample of the reservoir fluid from at least one sensor response on the optical instrumentation using an asymptote of a principal component analysis and equation of state;
perform a robust principal component analysis on the at least one sensor response; and
apply a robust regression method on the at least one sensor response, wherein the robust regression method is computed as $scores_{fit}=A+B \times v^{\beta}$, where A and B are constants determined by a regression method, $v$ is a formation fluid pumpout accumulated volume, and $\beta$ is a density decay rate.

* * * * *

UNITED STATES PATENT AND TRADEMARK OFFICE
CERTIFICATE OF CORRECTION

PATENT NO. : 11,371,345 B2
APPLICATION NO. : 16/488919
DATED : June 28, 2022
INVENTOR(S) : Peter Ojo Olapade, Bin Dai and Christopher Michael Jones It is certified that error appears in the above-identified patent and that said Letters Patent is hereby corrected as shown below:

In the Claims

In the Column 12, Line 41, Claim 6, and Line 56, Claim 10, In the Column 13, Line 35, Claim 20, In the Column 14, Line 14, Claim 21, and Line 39, Claim 22, each occurrence of "$X\ v^{\beta}$" should be -- $X\ v^{-\beta}$ --.

Signed and Sealed this
Fourth Day of October, 2022

Katherine Kelly Vidal
*Director of the United States Patent and Trademark Office*